United States Patent
Lucio

(10) Patent No.: US 11,103,606 B2
(45) Date of Patent: Aug. 31, 2021

(54) DEVICE AND METHOD FOR DISINFECTING CPAP COMPONENTS USING CHEMICALLY REACTIVE SUBSTRATE

(71) Applicant: 3B Medical, Inc., Winter Haven, FL (US)

(72) Inventor: Albert A. Lucio, Haines City, FL (US)

(73) Assignee: 3B Medical, Inc., Winter Haven, FL (US)

( * ) Notice: Subject to any disclaimer, the term of this patent is extended or adjusted under 35 U.S.C. 154(b) by 213 days.

(21) Appl. No.: 16/378,662

(22) Filed: Apr. 9, 2019

(65) Prior Publication Data
US 2019/0336627 A1   Nov. 7, 2019

Related U.S. Application Data

(60) Provisional application No. 62/665,549, filed on May 2, 2018.

(51) Int. Cl.
| | | |
|---|---|---|
| *A61L 2/10* | (2006.01) | |
| *A61L 2/20* | (2006.01) | |
| *A61M 16/06* | (2006.01) | |
| *A61M 16/08* | (2006.01) | |

(52) U.S. Cl.
CPC ............... *A61L 2/10* (2013.01); *A61L 2/20* (2013.01); *A61L 2/208* (2013.01); *A61L 2202/11* (2013.01); *A61L 2202/14* (2013.01); *A61L 2202/15* (2013.01); *A61L 2202/24* (2013.01); *A61M 16/06* (2013.01); *A61M 16/0875* (2013.01); *A61M 2209/10* (2013.01)

(58) Field of Classification Search
CPC ... A61L 2/10; A61L 2/20; A61L 2/202; A61L 2/208; A61L 2/24; A61L 2202/11; A61L 2202/122; A61L 2202/15; A61L 2202/24
See application file for complete search history.

(56) References Cited

U.S. PATENT DOCUMENTS

| | | | |
|---|---|---|---|
| 9,358,316 B2 * | 6/2016 | Leyva | A61L 2/183 |
| 10,076,582 B1 * | 9/2018 | Liao | A61L 2/088 |

FOREIGN PATENT DOCUMENTS

| | | | | |
|---|---|---|---|---|
| GB | 2498541 A | * | 7/2013 | A61L 2/232 |

OTHER PUBLICATIONS

Howard III, George B., "Executive Summary, CleanPAP," Triple Cs, LLC, Mr. Pior "Peter" Czapla, inventor. 2019.

* cited by examiner

*Primary Examiner* — Timothy C Cleveland
(74) *Attorney, Agent, or Firm* — Carlson, Gaskey & Olds, P.C.

(57) ABSTRACT

This disclosure relates to a device and method for disinfecting CPAP components using a chemically reactive substrate. Specifically, the device and method are used to disinfect CPAP components (or, CPAP equipment), including the various parts of a CPAP system, such as hoses, masks, pillows, couplings, humidifiers, etc., that require frequent cleaning and disinfecting. An exemplary device includes, among other things, a chamber, an ultraviolet (UV) light configured to emit UV light within the chamber, and a substrate chemically reactive to the UV light. Exposing the substrate to UV light releases free radicals which are configured to destroy bacteria, mold, and fungus, as well as eliminate odor. The free radicals may be circulated within the chamber and consequently within the CPAP components that are placed within the chamber to provide a thorough disinfection.

20 Claims, 5 Drawing Sheets

DEVICE AND METHOD FOR DISINFECTING CPAP COMPONENTS USING CHEMICALLY REACTIVE SUBSTRATE

RELATED APPLICATIONS

This application claims the benefit of U.S. Provisional Application No. 62/665,549, filed May 2, 2018, which is herein incorporated by reference in its entirety.

TECHNICAL FIELD

This disclosure relates to a device and method for disinfecting CPAP components using a chemically reactive substrate.

BACKGROUND

Continuous positive airway pressure (CPAP) represents a treatment for patients with breathing problems. Such problems typically manifest themselves at night while the patient is asleep. One such problem is sleep apnea.

The CPAP treatment uses mild air pressure to keep airways open, particularly when a patient is sleeping. CPAP systems have several components. The first is a flow generator, which is essentially a pump that creates a stream of air. Many flow generators include a humidifier, which is typically attached to the flow generator or integrally formed with the same. Humidifiers are configured to heat and moisten the air flow from the flow generator, which reduces the likelihood that a patient will experience discomfort from breathing dry air for a prolonged period. CPAP systems also include a conduit (i.e., a tube or hose) fluidly coupling a mask apparatus to the flow generator. The mask is affixed to the mouth and/or nose of a patient. Additionally, CPAP systems include various couplings, fittings, seals, valves, etc., that establish the fluid connection between the flow generator and the patient.

During use over the course of days, weeks, and months, it is recommended that the components of a CPAP system be cleaned and disinfected to prevent buildup of bacteria, for example. Disinfection is recommended to reduce health risks. CPAP systems and their associated components are typically cleaned manually by a patient using soap and water.

SUMMARY

A device for disinfecting components of a continuous positive airway pressure (CPAP) system according to an exemplary aspect of the present disclosure includes, among other things, a chamber, an ultraviolet (UV) light configured to emit UV light within the chamber, and a substrate chemically reactive to the UV light.

In a further non-limiting embodiment of the foregoing device, the substrate includes titanium oxide ($TiO_2$), and exposure of the substrate to the UV light releases free radicals.

In a further non-limiting embodiment of any of the foregoing devices, the free radicals include hydrogen peroxide (HO), hydroxyl radicals (OH), and hydroxides ($OH^-$).

In a further non-limiting embodiment of any of the foregoing devices, the device includes a blower configured to circulate the free radicals within the chamber.

In a further non-limiting embodiment of any of the foregoing devices, the device includes a tray having a first surface for supporting at least one CPAP component.

In a further non-limiting embodiment of any of the foregoing devices, the UV light and substrate are on an opposite side of the first surface as the at least one CPAP component.

In a further non-limiting embodiment of any of the foregoing devices, the substrate is provided by a mesh positioned between the UV light and the tray.

In a further non-limiting embodiment of any of the foregoing devices, the device includes an outer housing with a lid hingedly connected to the remainder of the outer housing.

In a further non-limiting embodiment of any of the foregoing devices, at least one of the lid and the outer housing includes a semi-circular recess to allow a CPAP conduit to pass from the chamber outside the device.

In a further non-limiting embodiment of any of the foregoing devices, the UV light emits one of UV-A light and UV-C light.

In a further non-limiting embodiment of any of the foregoing devices, the device is configured to run a predefined disinfection cycle when a lid of the device is closed.

In a further non-limiting embodiment of any of the foregoing devices, the device does not include any input buttons.

In a further non-limiting embodiment of any of the foregoing devices, the device includes only one input button, and the one input button is an on button.

In a further non-limiting embodiment of any of the foregoing devices, an outer housing of the device is shaped substantially as a polyhedron and includes a substantially flat bottom surface.

A method for disinfecting a component of a continuous positive airway pressure (CPAP) system according to an exemplary aspect of the present disclosure includes, among other things, directing ultraviolet (UV) light onto a substrate chemically reactive to the UV light such that the substrate releases free radicals, and circulating the free radicals within a chamber containing at least one CPAP component.

In a further non-limiting embodiment of the foregoing method, the free radicals are circulated through the normal operational pathway of the at least one CPAP component.

In a further non-limiting embodiment of any of the foregoing methods, the at least one CPAP component includes a mask and a conduit attached to the mask, and the free radicals are circulated within the mask and through the conduit.

In a further non-limiting embodiment of any of the foregoing methods, the at least one CPAP component includes a mask and a conduit, and the free radicals are circulated within the mask and through the conduit.

In a further non-limiting embodiment of any of the foregoing methods, the method includes running a predefined disinfection cycle when a lid of a device is closed.

In a further non-limiting embodiment of any of the foregoing methods, the step of running the predefined disinfection cycle does not require a user to press any input buttons.

BRIEF DESCRIPTION OF THE DRAWINGS

In FIG. 3, a lid is in an open position.

FIG. 4 illustrates a tray of the device. In FIG. 4, a UV light, which is arranged beneath the tray, is shown in phantom.

FIG. 5 illustrates a substrate, which is partially fragmented for purposes of showing the arrangement of a UV light beneath the substrate.

FIG. 6 illustrates a blower.

DETAILED DESCRIPTION

This disclosure relates to a device and method for disinfecting CPAP components using a chemically reactive substrate. Specifically, the device and method are used to disinfect CPAP components (or, CPAP equipment), including the various parts of a CPAP system, such as hoses, masks, pillows, couplings, humidifiers, etc., that require frequent cleaning and disinfecting. An exemplary device includes, among other things, a chamber, an ultraviolet (UV) light configured to emit UV light within the chamber, and a substrate chemically reactive to the UV light. Exposing the substrate to UV light releases free radicals which are configured to destroy bacteria, mold, and fungus, as well as eliminate odor. The free radicals may be circulated within the chamber and within the CPAP components that are placed within the chamber to provide a thorough disinfection.

Figure 1:
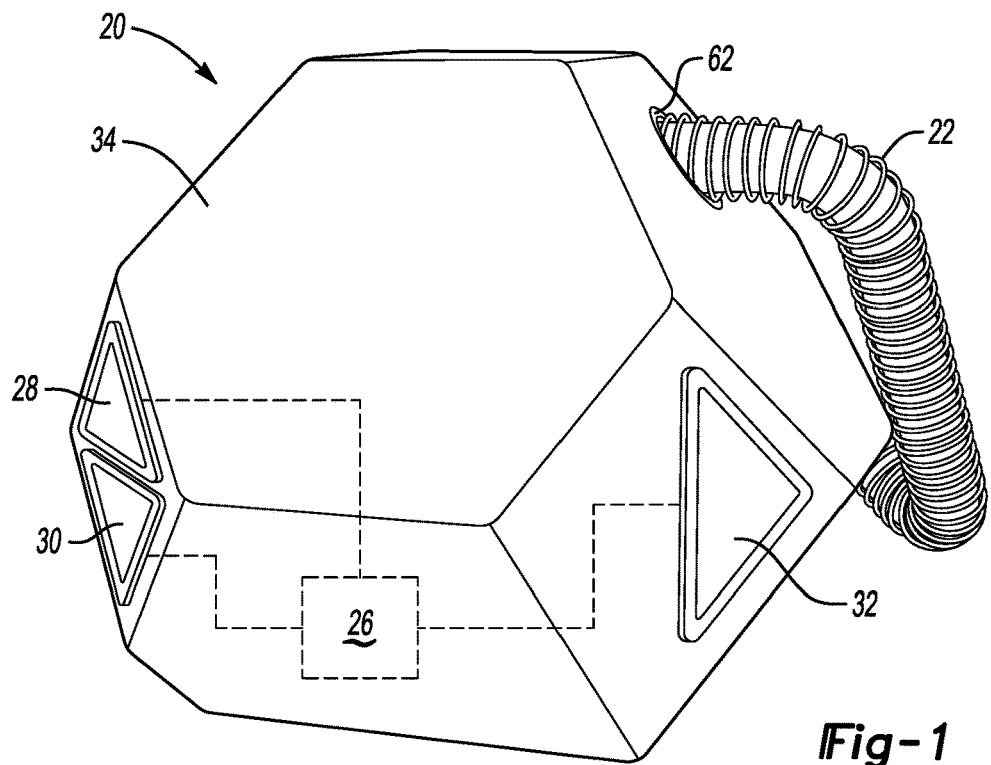
FIG. 1 illustrates an example device for disinfecting CPAP components from a front-perspective view. Certain aspects of the device are illustrated schematically.
Figure 3:
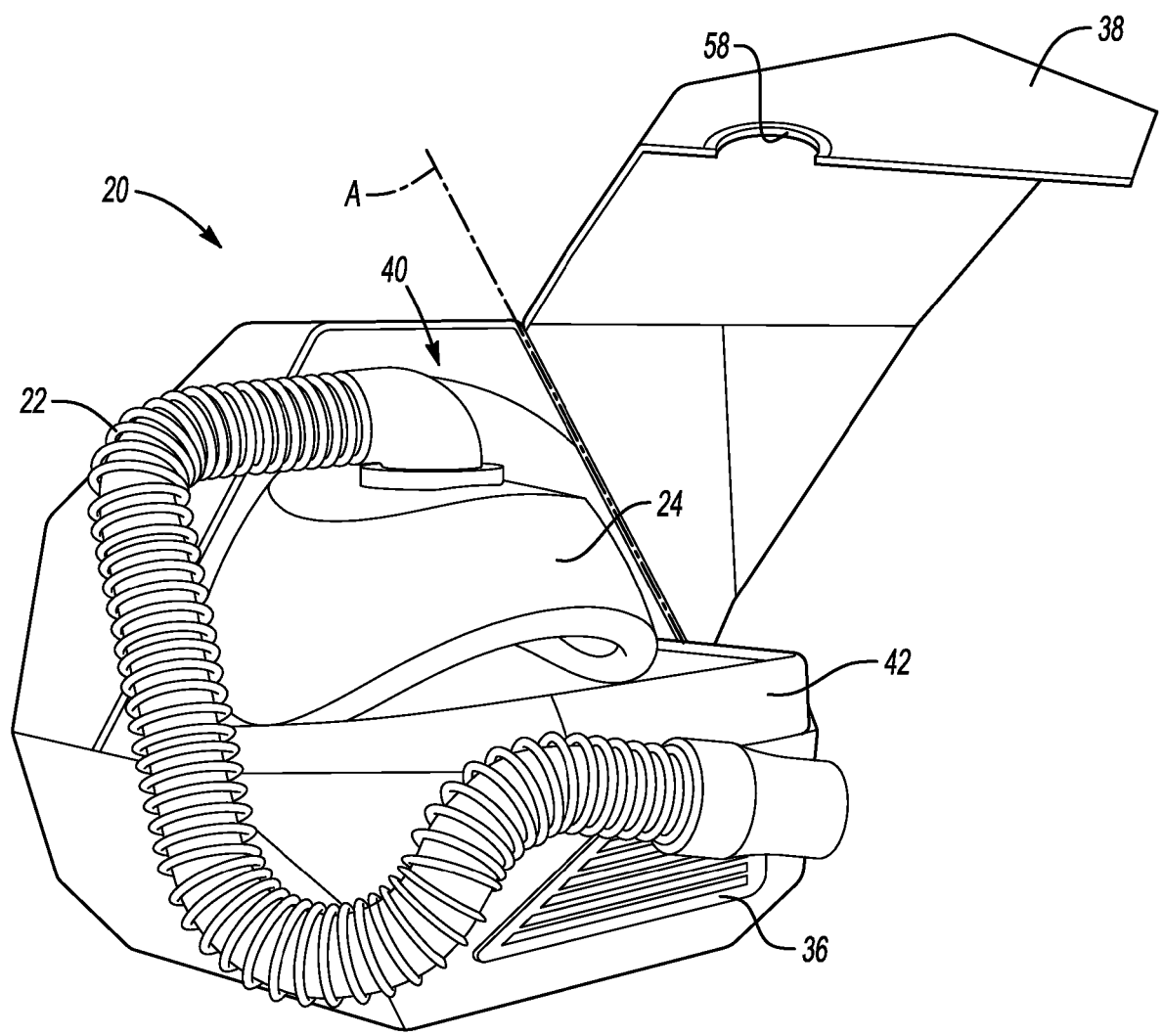
FIG. 3 illustrates the device of FIG. 1 from a rear-perspective view.

FIG. 1 illustrates an example device 20 for disinfecting CPAP components from a front-perspective view. In FIG. 1, a hose 22 is partially arranged within the device 20. As shown in FIG. 3, the hose 22 is attached to a mask 24, which is placed entirely within the device 20. While a hose 22 and mask 24 are shown in the figures, it should be understood that the device 20 may be used to disinfect other types of CPAP components, and may also be used outside the context of CPAP components to disinfect other items, such as other medical, dental, and hygiene-related products, such as toothbrushes, hearing aids, dentures, pacifiers, etc.

The device 20 includes a plurality of electromechanical components electrically connected to a control unit 26. The control unit 26 is illustrated schematically. The control unit (sometimes called a "controller") 26 may be programmed with executable instructions for interfacing with and operating the various components of the device 20, including but not limited to those shown in the figures and discussed herein. It should also be understood that the control unit 26 may additionally include a combination of hardware and software, and specifically may include a processing unit and non-transitory memory for executing the various control strategies and modes of the device 20.

In the example of FIG. 1, the device 20 includes a plurality of input buttons 28, 30, 32. While three input buttons are shown in FIG. 1, it should be understood that the device 20 may include additional or fewer input buttons. The input buttons 28, 30, 32 are not required in all examples. When present, the input buttons 28, 30, 32 allow a user to customize certain operating parameters of the device 20. Such customization may be particularly useful in laboratory settings, where users are trained to set these parameters. This disclosure also relates to a device, such as that shown in FIG. 7B, which does not allow a user to set any operating parameters. The latter device may be more user friendly from the perspective of some users, and may be more applicable for residential applications.

Figure 2:
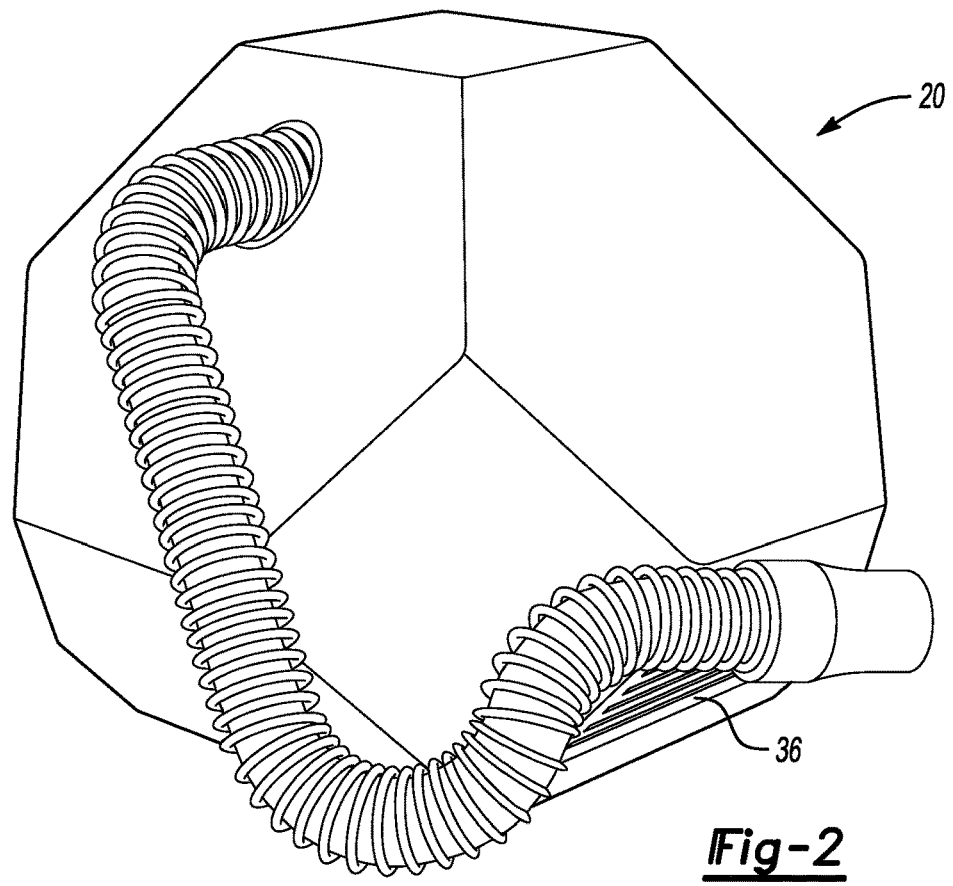
FIG. 2 illustrates the device of FIG. 1 from a rear-perspective view.

The device 20 includes an outer housing 34. In this example, the outer housing 34 is shaped as a polyhedron, which is a three dimensional shape with a plurality of flat, polygonal faces. The shape of the outer housing 34 provides a substantially flat bottom surface to allow the device 20 to rest on a table or counter top, for example. The outer housing 34 may be integrally formed as a single piece of plastic material with the exception of a vent 36 (FIG. 2) and a lid 38, which is hingedly connected to the remainder of the outer housing 34 and rotatable between an open position (e.g., FIG. 3) and a closed position (e.g., FIG. 2).

In FIG. 3, the lid 38 has been rotated to the open position by rotating about an axis A. The axis A is a hinge connection between adjacent flat faces of the outer housing 34. When the lid 38 is open, a chamber 40 of the device 20 is accessible. In this example, with the lid 38 open, a user has placed a hose 22 and mask 24 into the chamber 40. The mask 24 rests on a tray 42 within the chamber 40.

Figure 4:
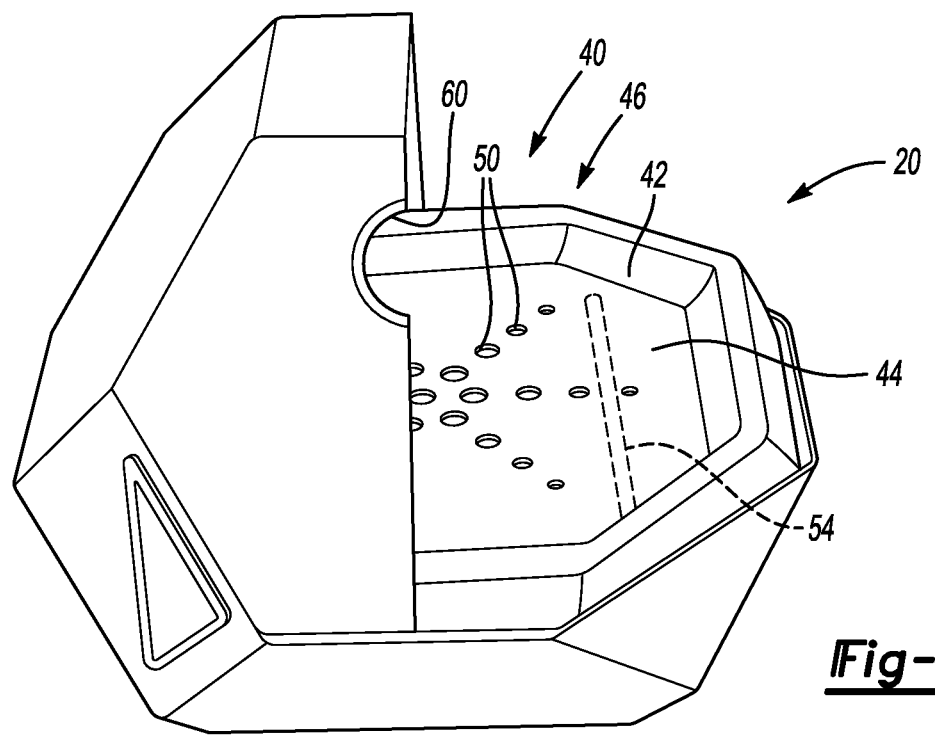
FIG. 4 is a top-perspective view of the device of FIG. 1 with the lid removed for ease of reference.
Figure 5:
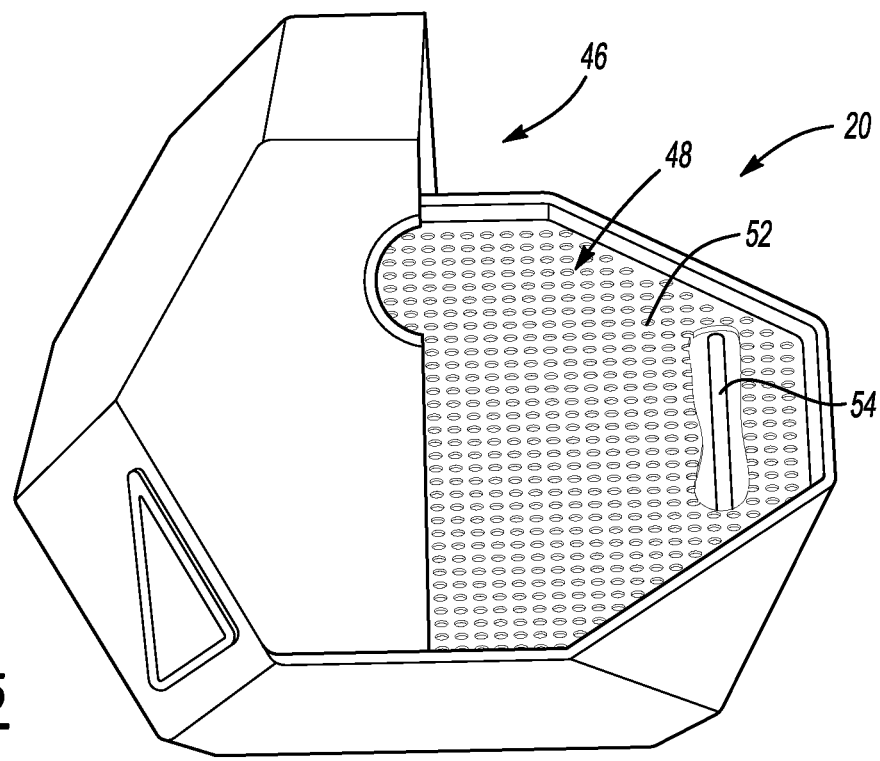
FIG. 5 is a top-perspective view of the device of FIG. 1 with the tray removed for ease of reference.

The tray 42 is perhaps best seen in FIG. 4, which does not show the hose 22, mask 24, or lid 38 for ease of reference. The tray 42 has a first surface 44, which is an upper surface in this example, for supporting at least one CPAP component, such as the hose 22 and/or the mask 24. The tray 42 essentially separates the chamber 40 into an upper portion 46 and a lower portion 48 (FIG. 5). Generally, the CPAP components to be disinfected are supported by the tray 42 within the upper portion 46 of the chamber 40. The tray 42 has a plurality of orifices 50 allowing fluid to flow from the lower portion 48 to the upper portion 46.

FIG. 5 illustrates the device 20 from a similar view as FIG. 4, but now with the tray removed. FIG. 5 illustrates a chemically reactive substrate 52 ("substrate" 52) and an ultraviolet (UV) light 54 adjacent the substrate 52. The substrate 52 includes a plurality of orifices and is provided by a mesh in this example. Specifically, the substrate 52 is provided by a metallic wire mesh material. The substrate 52 may be provided by other arrangements, such as screens or metal screens, and this disclosure is not limited to mesh. The substrate 52 may be removable from the device 20 in some examples. In FIG. 5, the substrate 52 is shown partially fragmented only for purposes of showing the UV light 54 beneath the substrate.

In one example of this disclosure, the substrate 52 includes titanium oxide ($TiO_2$), and exposure of the substrate 52 to UV light emitted from the UV light 54 releases free radicals from the titanium oxide ($TiO_2$). Example free radicals include hydrogen peroxide (HO), hydroxyl radicals (OH), and hydroxides ($OH^-$), for example. These free radicals mineralize and decompose undesirable compounds, such as bacteria, mold, and fungus.

The substrate 52 may be made of aluminum (Al) and coated with a coating containing or consisting entirely of titanium oxide ($TiO_2$) particles or nanoparticles. Instead of aluminum (Al), the substrate 52 may be made of another material that is coated with a coating containing or consisting entirely of titanium oxide ($TiO_2$). The other material may be a nonwoven material, polyester, or spun fiberglass, as examples. Regarding the coating, the substrate 52 may be coated with a combination of silver (Ag) and titanium oxide ($TiO_2$) particles or nanoparticles. In another example, the substrate 52 may be coated with a combination of titanium oxide ($TiO_2$) and magnesium oxide (MgO) particles or nanoparticles. These are examples only. This disclosure extends to other types of chemically reactive substrates.

While only one UV light 54 is shown in FIG. 5, it should be understood that the device 20 may include additional UV lights. Further, the UV light 54 emits one of UV-A light and UV-C light in this example. The UV light 54 is electrically connected to and selectively activated in response to instructions from the control unit 26. The UV light 54 in this example is provided by a light source, specifically a UV bulb (sometimes called a "UV lamp"), which is configured to emit UV light. The UV light 54 may be provided by a 13 Watt UV-C bulb, in one example. In other examples, the UV light 54 is provided by a bulb within a range of 5 to 20 Watts.

In a particular example, the UV light 54 is configured to emit UV-C light, which is a subtype of UV light especially suited for disinfection. Specifically, UV-C is relatively short-wavelength UV light, which is known to kill or inactivate microorganisms such as bacteria. In one example, the UV light 54 emits UV light at a wavelength within a range of 250 to 270 nanometers (nm), and in one particular example the UV light has a wavelength of 254 nm. Again, however, this disclosure is not limited to UV-C light, and extends to other types of light, such as UV-A light, which has a photocatalytic effect relative to the substrate 52. The UV light itself may also kill or inactivate the microorganisms and bacteria within the chamber 40. To this end, the tray 42 may be made of a transparent material.

Figure 6:
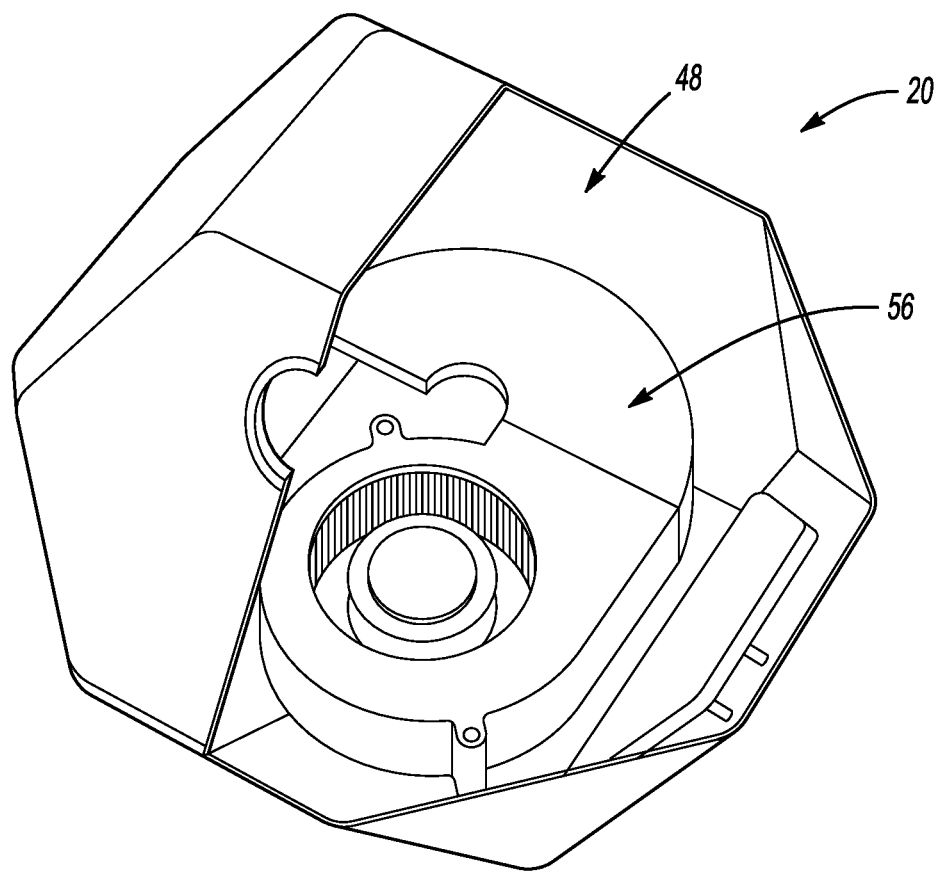
FIG. 6 is a top-perspective view of the device of FIG. 1 with the UV light and the substrate removed for ease of reference.

The released free radicals may have a relatively short half-life, such as on the order of a few seconds. With reference to FIG. 6, the device 20 includes a blower 56, such as a fan, configured to circulate airflow, and in turn the free radicals, within the chamber 40. The blower 56 is electrically connected to and responsive to instructions from the control unit 26. The blower 56 is shown somewhat schematically in FIG. 6. The blower 56 may be positioned beneath the substrate 52 and adjacent the UV light(s) 54. The blower 56 may draw air from the vent 36 and circulate that air within the chamber 40.

Operating the blower 56 as the free radicals are released from the substrate 52 causes the free radicals to circulate from the lower portion 48 of the chamber 40, through the orifices 50, and into the upper portion 46 of the chamber 40. The free radicals then circulate within and through the CPAP components within the chamber 40. For example, the blower 56 may generate airflow sufficient to cause the free radicals to circulate within the normal operational pathway of the CPAP component. That is, the free radicals flow through the same flow passage that is used during operation of a CPAP system. In the example of the hose 22 and mask 24, the free radicals flow through the mask 24 and along the interior of the hose 22. As such, the device 20 achieves thorough disinfection of the hose 22 and mask 24. The device 20 is especially configured to disinfect the portions of the CPAP components that see the most use, and hence the greatest potential buildup of bacteria, mold, and/or fungus.

With reference to FIGS. 3 and 4, the device 20 may include a circular or semi-circular recess to allow a hose to pass from the chamber 40 to a location outside the device 20. In this example, the lid 38 includes a semi-circular recess 58 (FIG. 3) configured to align with a semi-circular recess 60 (FIG. 4) formed in the outer housing 34 when the lid 38 is closed. As shown in FIG. 1, the alignment of these recesses 58, 60 forms a circular recess 62 which allows the device 20 to readily accommodate the hose 22. The circular recess 62 is optional, and is not required in all examples.

Figure 7A:
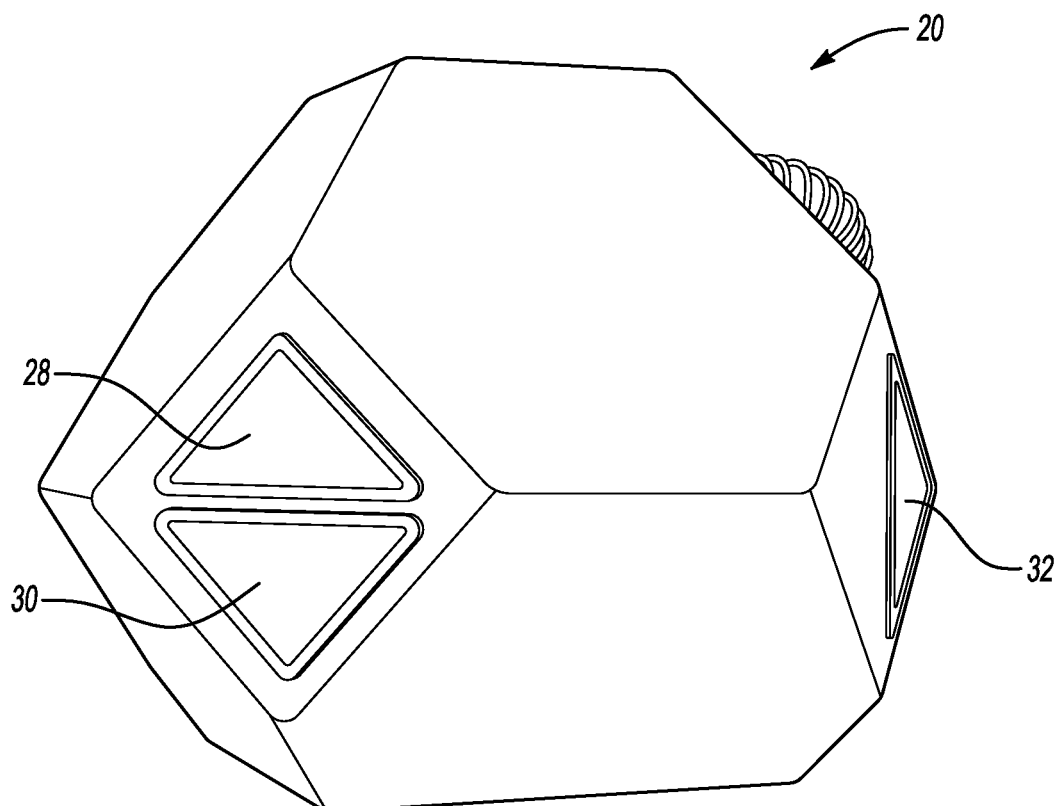
FIG. 7A is a front-perspective view of the device of FIG. 1.
Figure 7B:
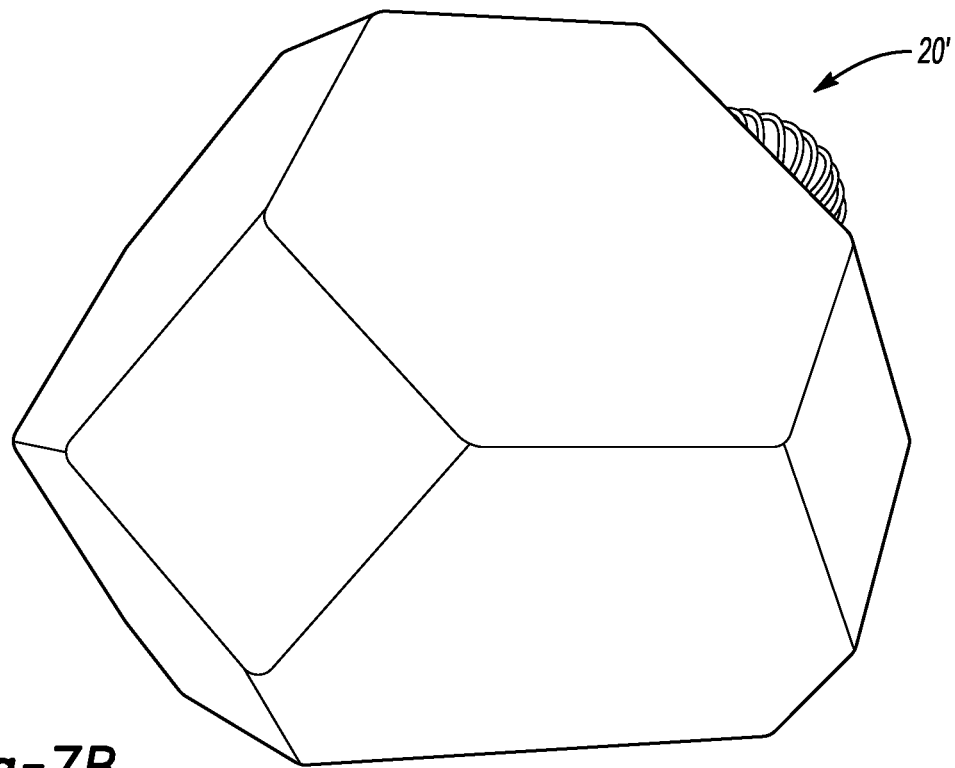
FIG. 7B is a front-perspective view of another example device.

FIGS. 7A and 7B illustrate two example devices 20, 20', respectively. As generally mentioned above, the device 20 of FIG. 7A may include a plurality of input buttons 28, 30, 32, which may control operation of the UV light, the blower, allow a user to set a cycle time, etc. In another example, shown in FIG. 7B, the device 20' is substantially similar to the device 20 discussed relative to FIGS. 1-6, but does not include any input buttons.

The device 20', rather, is configured to run a predefined disinfection cycle when the lid 38 is closed, for example. Alternatively, the device 20' may simply include an "on" button, which, when depressed, begins a predefined disinfection cycle. The predefined disinfection cycle may be predetermined and set as a factory setting of the control unit 26. The predefined disinfection cycle may involve the control unit 26 activating the UV light 54 and the blower 56 for a period of time, such as 3 or 5 minutes, as examples.

It should be understood that directional terms such as "upper," "lower," "above," "below," etc., are used herein with reference to the orientation of the device 20 in the figures and should not be considered limiting. Further, it should be understood that terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A device for disinfecting components of a continuous positive airway pressure (CPAP) system, comprising:
   a chamber;
   an ultraviolet (UV) light configured to emit UV light within the chamber;
   a substrate chemically reactive to the UV light such that exposure of the substrate to UV light releases free radicals;
   a blower configured to operate while the UV light is activated and as the free radicals are being released, wherein the blower is configured to draw air into the device and to circulate air within the chamber such that the blower circulates the free radicals within the chamber; and
   a tray having a first surface for supporting at least one CPAP component, wherein the UV light, the substrate, and the blower are on an opposite side of the tray as the first surface.

2. The device as recited in claim 1, wherein the substrate includes titanium oxide (TiO2).

3. The device as recited in claim 2, wherein the free radicals include hydrogen peroxide (HO), hydroxyl radicals (.OH), and hydroxides (OH—).

4. The device as recited in claim 1, wherein the substrate is provided by a mesh positioned between the UV light and the tray.

5. The device as recited in claim 1, further comprising an outer housing with a lid hingedly connected to the remainder of the outer housing.

6. The device as recited in claim 5, wherein at least one of the lid and the remainder of the outer housing includes a semi-circular recess to allow a CPAP conduit to pass from the chamber to outside the device.

7. The device as recited in claim 1, wherein the UV light emits one of UV-A light and UV-C light.

8. The device as recited in claim 1, wherein the device is configured to run a predefined disinfection cycle when a lid of the device is closed.

9. The device as recited in claim 8, wherein the device does not include any input buttons.

10. The device as recited in claim 8, wherein the device includes only one input button, and the one input button is an on button.

11. The device as recited in claim 1, wherein an outer housing of the device is shaped substantially as a polyhedron and includes a substantially flat bottom surface.

12. The device as recited in claim 1, wherein:
the substrate is beneath the tray,
the UV light is beneath the substrate, and
the blower is beneath the substrate.

13. The device as recited in claim 12, wherein:
the tray divides the chamber into an upper portion above the tray and a lower portion beneath the tray,
each of the substrate, the UV light, and the blower is in the lower portion, and
the tray is configured to support at least one CPAP component in the upper portion.

14. The device as recited in claim 13, wherein the tray includes a plurality of orifices configured to allow fluid to flow from the lower portion to the upper portion.

15. The device as recited in claim 14, wherein the substrate includes a plurality of orifices.

16. The device as recited in claim 14, wherein the tray is made of a transparent material.

17. A system for disinfecting components of a continuous positive airway pressure (CPAP) system, comprising:
a mask and a conduit attached to the mask;
a device, comprising:
a chamber;
a tray dividing the chamber into an upper portion above the tray and a lower portion beneath the tray, wherein an upper surface of the tray supports the mask within the upper portion, wherein the tray includes a plurality of orifices configured to allow fluid to flow from the lower portion to the upper portion, wherein the tray is made of a transparent material;
an ultraviolet (UV) light within the lower portion and configured to emit UV light within the chamber;
a substrate within the lower portion and chemically reactive to the UV light such that exposure of the substrate to UV light releases free radicals, wherein the substrate includes a plurality of orifices;
a blower within the lower portion, wherein the blower is configured to operate while the UV light is activated and as the free radicals are being released, wherein the blower is configured to draw air into the device and to circulate air within the chamber such that the blower circulates the free radicals within the chamber;
an outer housing with a lid hingedly connected to the remainder of the outer housing, wherein at least one of the lid and the remainder of the outer housing includes a semi-circular opening receiving the conduit such that the conduit passes from the chamber to outside the device.

18. The device as recited in claim 1, wherein the substrate includes a metallic wire mesh material.

19. The device as recited in claim 1, wherein the device includes a controller configured to activate both the UV light and the blower for a period of time.

20. The system as recited in claim 17, wherein the device includes a controller configured to activate the UV light and the blower for a period of time.

* * * * *